United States Patent [19]
Raynie et al.

[11] Patent Number: 5,551,879
[45] Date of Patent: Sep. 3, 1996

[54] DREAM STATE TEACHING MACHINE

[75] Inventors: Arthur D. Raynie; Raul G. Rodriguez; Gary L. Forister; Alexander B. Crawford, all of San Antonio, Tex.

[73] Assignee: Dream Weaver J.V., San Antonio, Tex.

[21] Appl. No.: 307,324

[22] Filed: Sep. 16, 1994

[51] Int. Cl.$^6$ ................................................. A61M 21/00
[52] U.S. Cl. ............................... 434/236; 600/26; 600/27
[58] Field of Search ..................................... 434/236–238; 446/419; 600/26–28; 128/731, 732

[56] References Cited

U.S. PATENT DOCUMENTS

| | | |
|---|---|---|
| 3,884,218 | 5/1975 | Monroe . |
| 4,735,199 | 4/1988 | DiLullo . |
| 4,832,050 | 5/1989 | DiLullo .............................. 446/419 X |
| 4,863,259 | 9/1989 | Schneider et al. . |
| 5,219,322 | 6/1993 | Weathers .................................... 600/27 |

OTHER PUBLICATIONS

Kaser, Vaughn A. "The Effects of an Auditory Subliminal Message Upon the Production of Images and Dreams", *The Journal of Nervous and Mental Disease*, vol. 174, No. 7 (1986), 397–407.

LaBerge, Stephen P. "Lucid Dreaming as a Learnable Skill: A Case Study", *Perceptual and Motor Skills*, 51 (1980), 1039–1042.

LaBerge, Stephen P., Lynn E. Nagel, William C. Dement, and Vincent P. Zarcone, Jr. "Lucid Dreaming Vertified by Volitional Communication During REM Sleep", *Perceptual and Motor Skills*, 52 (1981), 727–732.

LaBerge, Stephen, Ph.D. *Lucid Dreaming* (New York: Ballantine Books, 1986), pp. 161–162.

LaBerge, Stephen, Ph.D. and Howard Rheingold. *Exploring the World of Lucid Dreaming* (New York: Ballantine Books, 1990).

Sergio, W. "Use of DMAE (2–dimethylaminoethanol) in the Induction of Lucid Dreams", *Medical Hypotheses* 26 (1988), 255–257.

Tholey, Paul. "Techniques for Inducing and Manipulating Lucid Dreams", *Perceptual and Motor Skills*, 57 (1983), 79–90.

*Primary Examiner*—Richard J. Apley
*Assistant Examiner*—Glenn E. Richman
*Attorney, Agent, or Firm*—Gunn, Lee & Miller, PC

[57] ABSTRACT

A device for enhancing lucidity in the dream state of an individual. The device includes electronic circuitry incorporated into a headband for the user to wear while sleeping. The circuitry includes a detector for fitting adjacent to the eye of the sleeping individual, for detecting Rapid Eye Movement (REM), which occurs during the dream state. The detector emits a signal that is evaluated by additional circuitry to determine whether or not REM sleep is occurring. If REM sleep is occurring, a signal is generated to operate a recorded, which typically plays prerecorded messages through the headphones engaging the ear of the sleeping individual.

23 Claims, 6 Drawing Sheets

DREAM STATE TEACHING MACHINE

FIELD OF THE INVENTION

A device for aiding and inducing lucid dream states through detecting REM sleep and providing a prerecorded message responsive to the dream state without waking the sleeping individual.

BACKGROUND OF THE INVENTION

Lucid dreaming is the ability to be aware of the experience of dreaming, while in a dream state. This phenomenon occurs when an individual in the dream state, and without awakening, realizes that he/she is dreaming.

During "lucid dreams" the individual is remarkably wakeful—although still asleep. The individual can reason clearly, remember freely, signal that he/she is conscious, and may even change the plot of his/her dream if so desired. The natural and spontaneous occurrence of this phenomenon has been reported by different individuals throughout history. To this date, there is little controversy about the "reality" of lucid dreaming.

In the recent past, lucid dreaming has been the subject of scientific inquiry and validation by different scientists. Dr. Stephen Laberge, Director of the Sleep Research Center of the Stanford University School of Medicine, has contributed to the popularization and understanding of this phenomenon. An important contribution by Dr. Laberge is that lucid dreaming can be taught to any individual willing to be trained and motivated enough to practice diligently. Dr. Laberge reported about this ability in his paper: "Lucid Dreaming as a Learnable Skill: A Case Study" *Perceptual and Motor Skills*, (1980) 51, 1039–1042.

The present invention relates to an apparatus for detection of rapid eye movement (REM) during sleep to help induce lucid dreaming. More specifically, a dream state detection device described herein provides a mechanism whereby REM is detected during sleep, and, using a prerecorded cuing message, the user is taught to recognize the dream state and become lucid whenever it occurs.

Becoming lucid while dreaming is in itself an exhilarating experience and may be used for educational purposes. The problem with lucidity is it often happens on its own with little or no means of consciously inducing or controlling this state while dreaming.

It is applicants' objective to offer a device that will not only help induce the lucid state during REM sleep, but will also provide a means to direct a desired scenario and provide learning opportunities. The REM state of sleep offers a benefit for learning for, in learning to become lucid in REM sleep, one may also learn to utilize this dream state to experience any desired situation, to modify behavior, or to further enhance their personal evolution.

PRIOR ART

Different methods and techniques have been developed to help the induction of lucid dreaming. These include chemical compounds, like DMAE (2-dimethylaminoethanol), exercises in self awareness (visualization and meditation), and sensory stimulation (auditory, visual or tactile stimulation). These technologies and its results have been reported by Laberge in his book "Exploring the World of Lucid Dreaming" published by Ballantine Books in 1990.

Chemical: W. Sergio published an article entitled "Use of DMAE (2-dimethylaminoethanol) in the Induction of Lucid Dreams" Medical Hypotheses (1988), 26, 255–257. In this report, Sergio maintains the use of this food supplement aided in the induction of lucid dreaming by holding the user at a higher level of consciousness while sleeping.

Self Awareness: Several techniques using visualization and meditation have shown to be quite successful, as Paul Tholey reported in "Techniques for Inducing and Manipulating Lucid Dreams" Perceptual and Motor Skills, (1983), 57, 79–90.

Sensory Stimulation: Experiments have previously been conducted with apparatus-induced lucid dreams whereby the dreamers' senses are stimulated through visual, audible, or tactile stimulation, such as electric shock or vibration. All three methods have generated promising test results in the lab, as Stephen Laberge reported in "Exploring the World of Lucid Dreaming" Ballantine Books: New York (1990). A lucid dream-inducing apparatus presently available to the public has been developed by Stephen Laberge. His apparatus uses small LEDs positioned in a mask which, when REM is detected, flash in front of the eyes. This visual stimulation can be perceived by the sleeper as a cue to become lucid. The use of one's own voice in which the sleeping mind's "unconscious mind" is accustomed to is more accepted in the dream state. *Lucid Dreaming*, S. Laberge, (1986), pp. 161–162. The desired message is induced into the user wearable device by pressing a button located on our device and speaking into one of the earphones. Example: "John, you are dreaming. Check for reality cues." Other specific instructions, commands, or suggestions can be entered leading the dreamer into a desired situation.

The volume of one's own voice used as a cue or to instruct the dreamer is controlled by the user. The volume control is also designed to emit at a frequency below normal hearing range. "The Effects of an Auditory Subliminal Message Upon the Production of Images and Dreams" *The Journal of Nervous and Mental Disease*, (1986), Vol. 174, No. 7, pp. 397–407.

Research data on subliminal input advocates cognitive retention of information induced by subliminal means, even when induced at a high speed. In the dream state, the mind is more receptive to what it is told, even at the subliminal level. Some users may be more receptive than others; therefore, the subliminal input has been left as an option for the user.

What few devices of prior art that are available have focused on waking up the dreamer at some time after REM is detected. The stimuli associated with these methods would resemble that of an alarm clock. At best, a sound and/or lights may be utilized to arouse the dreamer from the dream state to an awakened state.

Applicants' device is superior to those of prior art, for applicants' teachings have far exceeded the concept of a REM alarm clock. Applicants' device is so designed that the user will not only become aware that he/she is dreaming without being awakened, but also having available to the dreamer predetermined instructions outlining a desired dream scenario. These instructions are orchestrated by the user.

SUMMARY OF THE INVENTION

The device comprises a dream (REM) determination circuit, an analog record and volume-controlled playback circuit, and a user-settable delay, allowing the individual to predetermine the time from determination of REM to the actual instant that the prerecorded message is relayed back to the user. This enables the user to use the device as an educational means and as a tool to gain the necessary fundamentals needed to be a proficient, lucid dreamer. An example of one of these fundamentals is dream recall. The device can be set with a delay of up to ten minutes. This amount of delay, coupled with a message aimed at awakening the dreamer from the dream, can, over a short time, build the necessary dream recall ability needed.

The REM detector and circuit is superior in that it checks for REM about once every minute and, therefore, is less likely to miss REM activity. It also has the capability of discriminating between right or left eye movement during the lucid sleep state. The eye position detection can be used by the lucid sleeper to control on-line communication peripherals or activate other devices associated with desired dream experiences. (See "Lucid Dream Verified By Volitional Communication During REM Sleep" *Perceptual and Motor Skills*, (1981) 52, 727–732.

The device is also equipped with a coupling jack, allowing further devices to be attached to work in conjunction with the main unit. One of these will be the interface with CD or audio tape. It will allow the use of advance technologies concerning hypnosis, relaxation, learning acceleration, subliminal messages, and others. These further developments would include a device that generates an oscillated tone aimed at controlling the stage of sleep the individual is in. An EEG machine has recorded such oscillation, and there, frequencies are related to the stages of waking and sleeping consciousness. The mind tends to match perceived oscillations such as this, allowing the device to put the user in the stage of sleep conducive to lucid dreaming.

DETAILED DESCRIPTION OF THE PREFERRED EMBODIMENT

Figure 1:
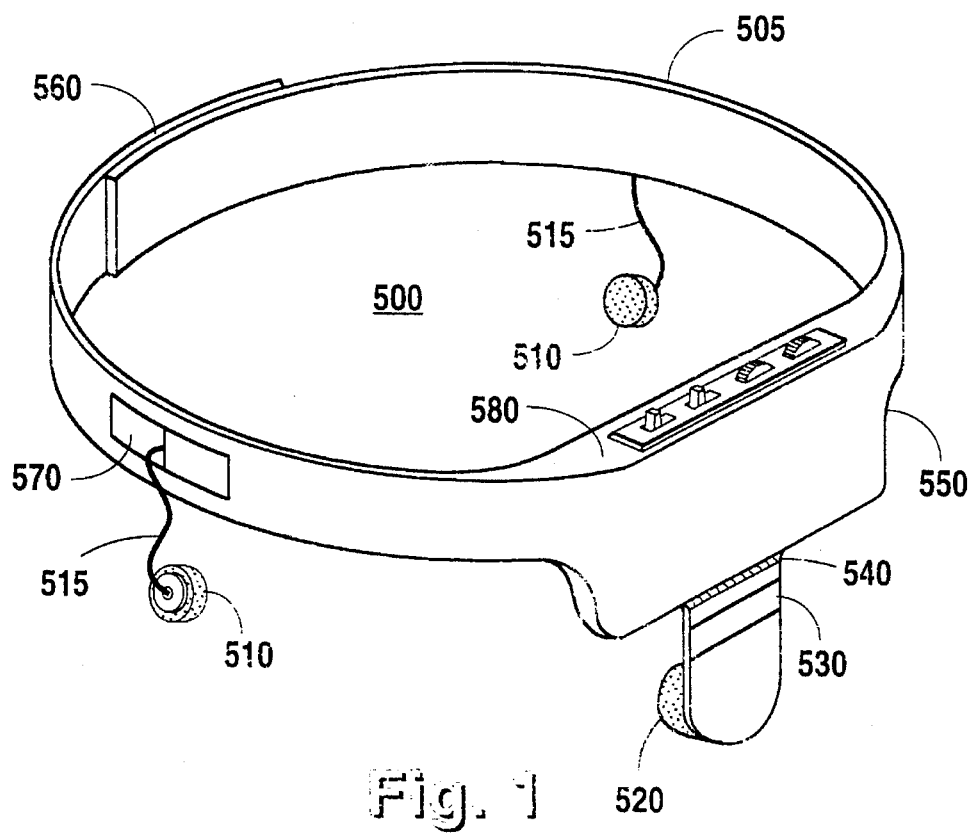
FIG. 1 is a perspective view of the present invention from the front.
Figure 2:
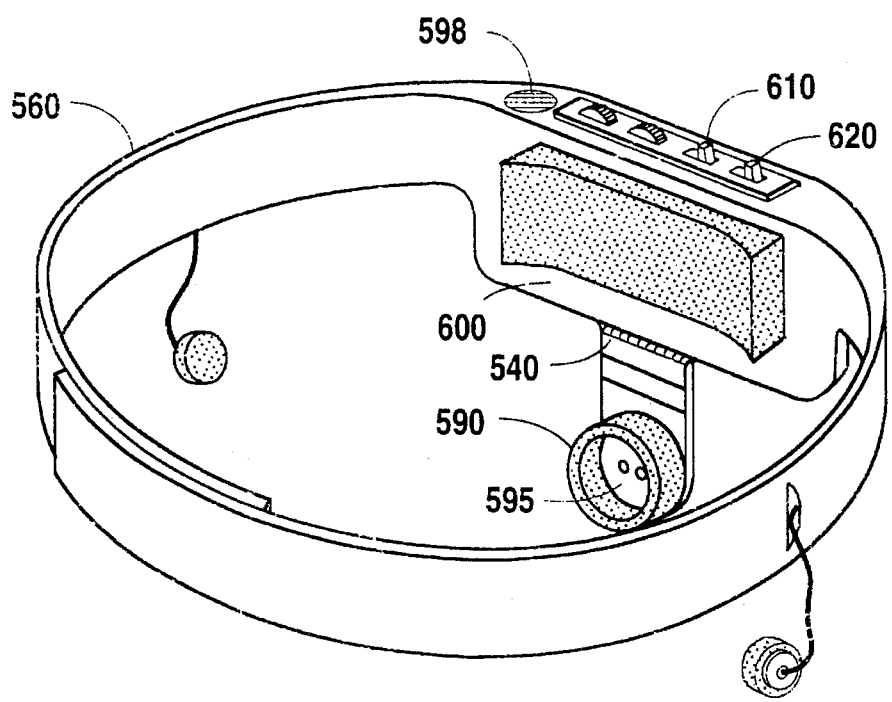
FIG. 2 is a perspective view of the present invention from the rear.

Referring now to FIG. 1 and FIG. 2, the dream state device 500 consists of an adjustable band 505 that fits around the head, similar to the sweat band that runners use, with Velcro®-type fastenings 560 at the rear. At each side of the band near the ears of the wearer is an earphone 510; Velcro® straps 570 are used to hold connecting wires 515 close to the head, while one earphone 510 is placed in each ear. Suspended from the front part of the band 505 is an eyepiece 520, which fits over one eye of the wearer and can be adjusted to move up and down using a mechanical friction fitting 530 so as to cover the eye completely. This eyepiece 520 is fitted with foam 590 or similar material to block out extraneous light when placed over the eye. In addition, the eyepiece 520 can be moved upward using a hinge 540 so that the band 505 can be worn without impeding sight.

Directly above the eye piece is a pouch 550 which holds electronics 580 that interact with the wearer via feedback from an eye movement sensor 595 within the eyepiece 520, the earphones 510, and a microphone 598. Padding 600 may be included around the inside periphery of the headband for additional user comfort.

The basic operation of the system is as follows. Before the user places the band 505 on his head, he turns on the power switch 610 to the electronics and records a cuing message by pressing the record button 620 located on the headband 505 and speaking either into the microphone 598 provided to record his own voice for a period of, typically, 2 to 20 seconds. The message will be recorded and stored by the electronics 580 within the headband pouch 550 for playback at a later time. In an alternative embodiment of the invention, either of the earphones 510 can be used in place of the microphone to record the cuing message when the record button 620 is depressed.

After recording the message, the wearer will then place the dream state device 500, by means of the headband 505, upon his head, securing it with the Velcro®-type fastenings 560 at the rear of the headband 505 so that the eyepiece 520 is located near one of the wearer's eyes. The eyepiece 520 is further adjusted so as to fit comfortably over the eye and the center of the eye piece is located proximate to the eyelid over the center of the eye socket. Each of the earphones 510 is placed into the wearer's ears, and the Velcro® straps 570 at the side of the headband are used to secure the earphone connecting wires 515 to the headband 505 to prevent entanglement when the wearer moves while sleeping.

The wearer will typically keep this headband 505 in place for the entire period of sleep. The eye movement sensor 595 is used to monitor eye movements and, aided by the electronics 580, to detect a particular kind of movement, commonly known as REM (rapid eye movement). This occurs at some frequency of movement, typically less than 10 hertz. The eye movement sensor 595 can be mechanical, using a small springboard-type platform made of a flexible material, such as plastic. Such a platform would be reflectively coated (e.g. with aluminum) so as to provide a surface which touches the eyelid gently and is able to reflect any small movements of the eyelid using an emitter/detector pair (or grouping) located in the eyepiece 520. The emitter/detector pair (or grouping) could operate by means of visible light, infra-red, ultrasound, or any other form of physical wave which would be affected by small movements of the eye beneath the eyelid. Also, eye movement can be detected directly by use of the emitter/detector pair without the use of an intervening mechanical reflector. The emitter and detector (or detectors) can be separate units located within the eyepiece 520 or combined into a single unit, such as the Phillips model number ECG3104. Multiple emitters, detectors, or emitter/detector pairs may also be used to detect specific eye movement and position.

Once REM has been detected by the electronics 580 and persists for some preselected amount of time (e.g. 2 to 10 seconds), or a preselected number of eyelid movements, the cuing message is played back through the earphones to the wearer. The cuing message can be recorded by the wearer or anyone before placing the apparatus on the wearer's head. A message recorded in the wearer's own voice would be less likely to disturb sleep, and more likely to result in alerting the wearer to the fact that he is now entering a dream state. This prerecorded message will typically consist of some kind of reality-check message, such as "Mr. X you are now dreaming. Check for reality clues." The purpose of the cuing message is to train the user to recognize the dream state and to become lucid while dreaming.

Figure 3:
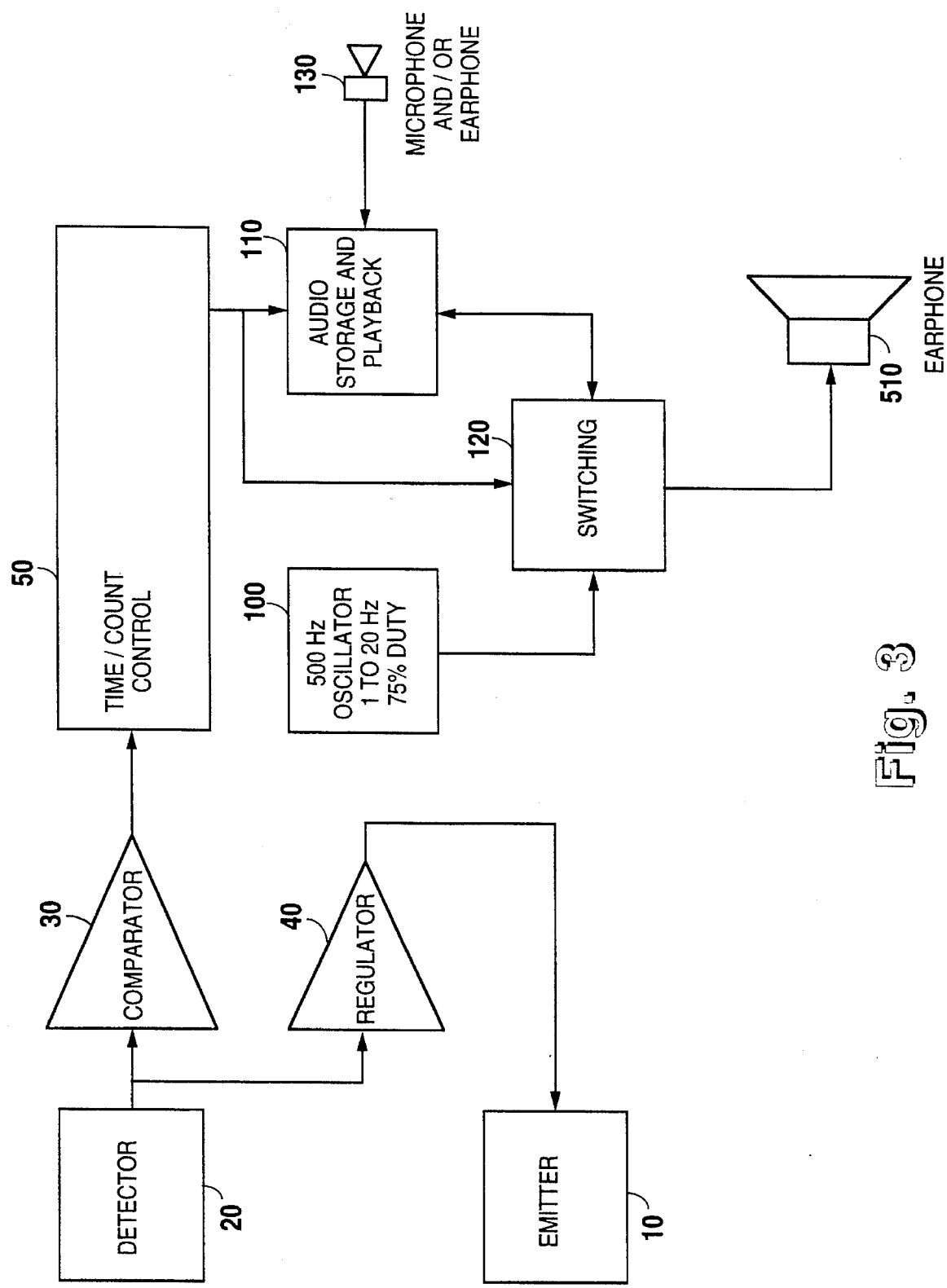
FIG. 3 is a functional diagram of the present invention.

Referring now to FIG. 3 (alternate preferred embodiment), the components of the electronics 580 consist of a detector 20, an emitter 10, a comparator 30, a regulator 40, and 4 timers (timer 1, timer 2, timer 3, and timer 4) contained in a time/count control module 50. Also included are an audio storage and playback module 110 which can record and play back audio introduced to the microphone 130, an oscillator 100, and a switching module 120 which allows audio playback through the earphone 140 from the oscillator 100, the audio storage and playback module 110, or both. The switching module 120 can also be used to allow one or both of the earphones 140 to function as a microphone during the cuing message recording period; or alternatively, a separate microphone 130 can be used to provide a signal directly into the audio storage and playback module.

In the preferred embodiment, all components (except the emitter/detector pair, earphones 510, and audio storage and playback 110) are integrated into a single microcircuit, such as a modified version of an Intel model number 80C51 microprocessor, or similar programmed device. However, in the following discussion, the components and modules comprising the electronics 580 will be discussed separately so their individual functions may be more readily understood.

Figure 4:
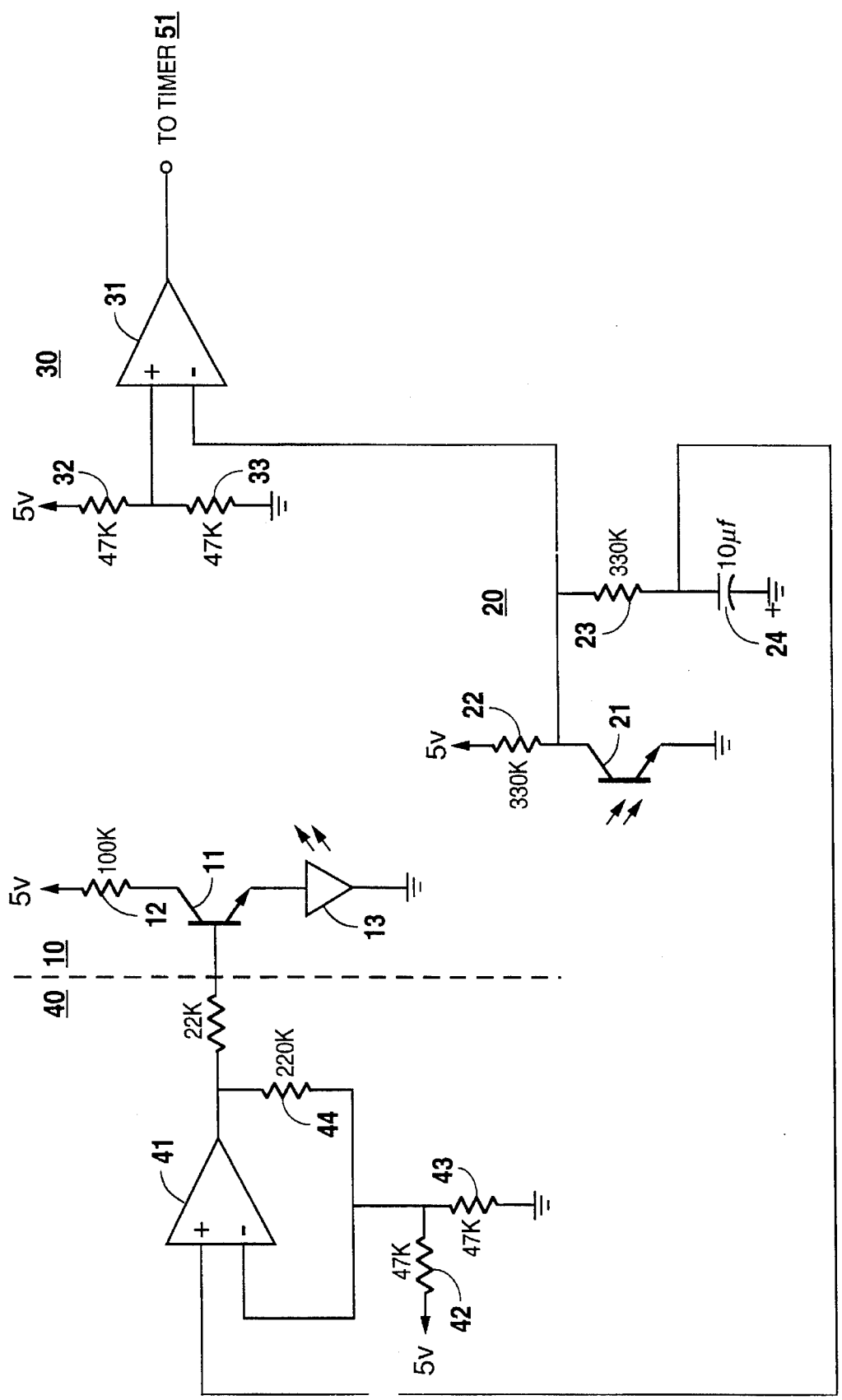
FIG. 4 is a schematic diagram of the emitter, detector, regulator, and circuitry as embodied in the present invention.

Referring now to FIG. 4, when power is first applied to the dream state device 500, there is no radiation provided by the emitter circuitry 10, which consists of an LED (light emitting diode) 13 whose current is modulated by a transistor 11 so as to provide turn-off and turn-on power to the LED 13. Current to the LED 13 is limited by the resistor 12. When LED 13 is in the off condition, the detector 20, which is connected to the regulator 40, provides a signal that, after some time delay produced by charging capacitor 24, causes the regulator 40 to bias transistor 11 so that LED 13 turns on. At this point, detector 20 will begin to sense radiation from LED 13 which will, in turn, reduce the voltage present at detector 20 and thereby reduce the brightness of LED 13. The purpose of regulator 40 is to adjust the output of LED 13 to compensate for varying distance to the eye or reflection mechanism as well as varying amounts of reflectivity from either the eye or coated reflector. That is, if the distance and reflectivity were fixed, the regulator circuitry 40 would not be necessary. Charging capacitor 24 and resistor 23 operate in combination with detector 20, regulator 40, and emitter 10 circuitry in order to provide delayed compensation for varying radiation levels.

Figure 5:
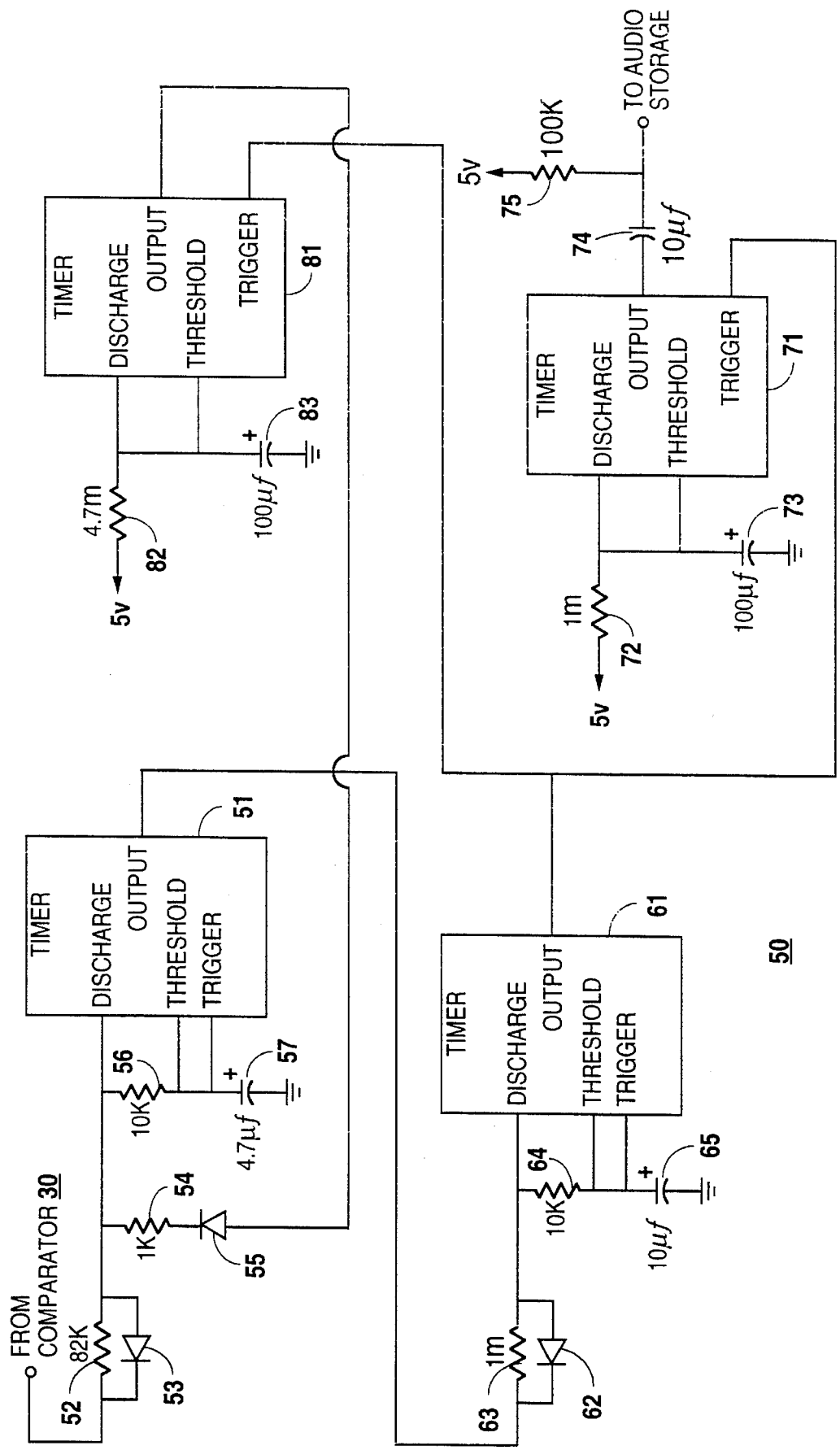
FIG. 5 is a schematic diagram of the timing circuitry as embodied in the present invention.

Once detector 20 senses eye movement, a signal is sent to the comparator circuitry 30, where it is compared against a fixed bias level produced by the combination of resistor 32 and resistor 33. Referring now to FIG. 4 and FIG. 5, when the bias level is exceeded, timer 51 is inhibited. When enabled, timer 51 cycles at a rate of approximately 0.25 hertz with a 50% duty cycle. When inhibited, the output remains at a constant +5 V level.

The output from timer 51 feeds into timer 61. When eye movement is sensed by comparator 30 and timer 51 is inhibited, timer 61 is allowed to complete its cycle, which lasts approximately 10 seconds. At the end of the timer 61 cycle, the output of timer 61 will go from a high (+5 V) level to pulse low for a fraction of a second. When there is no eye movement and the output from timer 51 is cycling, timer 61 provides no change in its output, i.e., the output stays at a high (+5 V) level.

When eye movement has been sensed and timer 61 has completed a cycle by pulsing its output low, timers 71 and 81 begin to cycle. Timer 71 has a cycle time of approximately 1 to 2 minutes, where the output begins at a high level and goes low at the end of the cycle. Timer 71 will cycle and produce a low level output if REM is detected for a period of, for example, 10 seconds or more, as indicated by the cycle time of timer 61. The end of the timer 71 cycle results in audio playback of the recorded cuing message. This message has been recorded by the wearer himself and reminds the dreaming person to check for reality clues and trains for lucidity. The length of the prerecorded message is variable, and may play for an indefinite amount of time.

Timer 81 is also allowed to cycle when an initiation pulse is presented by the output of timer 61. The cycle time for timer 81 lasts approximately 8 to 10 minutes. The output from timer 81 indirectly disables timer 61 by applying a rapidly cycling signal at the input of timer 51 (approximately 10 hertz) so that REM cannot enable the output of timer 51. This inhibition in turn disables timer 61. In the preferred embodiment of the invention, the output of timer 81 is used to disable all parts of the electronics 580 so as to conserve energy consumed.

Audio storage and playback module 110 functions are provided by a monolithic integrated circuit, such as the Information Storage Devices model number ISD 1020A integrated circuit. This device provides all functions for recording and playback of audio with a recording time range of up to 20 seconds.

An additional component of the electronics 580 within the headband pouch 550 is a relaxation-inducing circuit. The user is provided with a selectable audio frequency tone (e.g. 100 to 2000 hertz) which is modulated at a selectable rate of from 1 to 20 cycles per second. This circuitry provides a sound which is conducive to relaxation and occurs at approximately the same frequency as brainwaves (commonly known as Alpha, Beta, Delta, and Theta waves). The relaxation tone can be selected by the wearer to sound continuously throughout the sleeping state, to terminate on the occurrence of some event (e.g. REM detection), or to terminate after some predetermined amount of time has passed (time delay and then shutoff). As a final alternative, instead of terminating, the tone can be set to play at a reduced volume level, even below one's typical sound threshold (e.g., about 40 db lower than normal listening intensity, also known as "subliminal").

Figure 6:
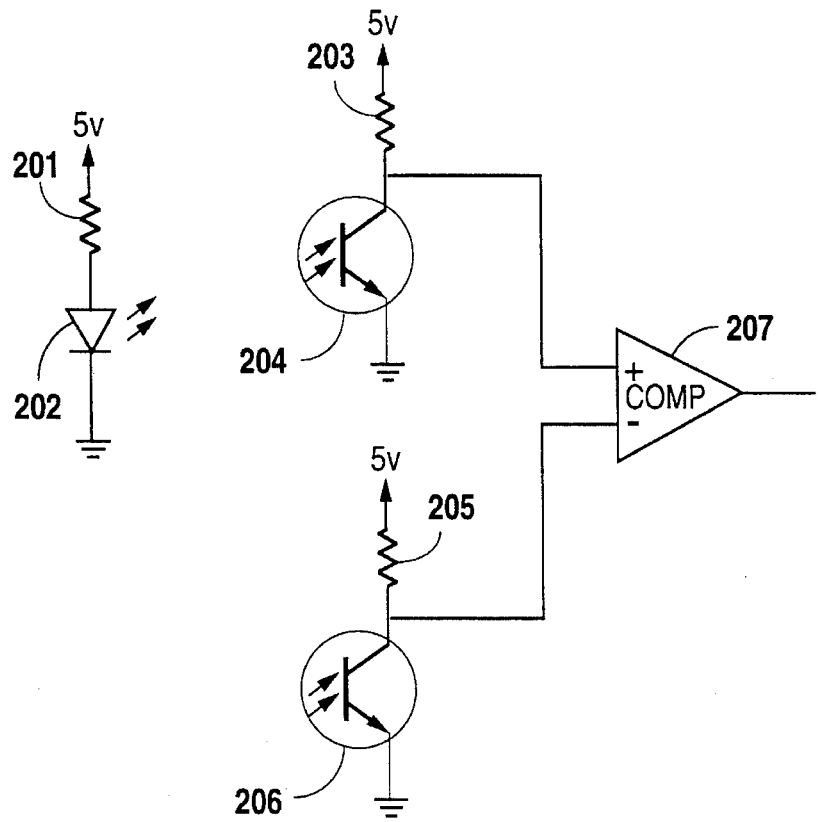
FIG. 6 is a schematic diagram of a preferred embodiment of REM detection circuitry in the present invention.

Referring now to FIG. 6, a preferred embodiment to the REM detection mechanism provided by detector 20, comparator 30, emitter 10, and regulator 40 illustrated in FIG. 4 is shown. In this variation, detector transistor 204 and detector transistor 206 both act to receive radiation (typically reflected from the closed eye of the user) from LED 202. The output brightness of LED 202 is not regulated, but is maintained at a constant level by bias resistor 201. Sensitivity of transistor detector 204 is set by the value of resistor 203, the sensitivity of transistor detector 206 is set by the value of resistor 205. The resulting currents from detector 204 and detector 206 are sent to comparator 207, which uses the difference between the two currents to produce an indication of eye movement as the output.

Detector transistors 204 and 206 may also be replaced by photo resistors, photodiodes, or solar cells. This embodiment is used to show how a multiplicity of detectors may be used, typically located symmetrically with respect to the emitter, for REM detection, as well as to discriminate; that is, to determine the direction the eye is looking (i.e., straight ahead, up, down, side-to-side). This is done with comparator (207) going low indicating the eye looking in one direction, going high indicating the eye looking in the other direction. In this manner, if the user becomes lucid in the sleep state, he may learn to selectively control, through repeated controlled eye movement (for example, in one direction), the playing of prerecorded messages or other sounds, or to otherwise interface with the device.

Figure 7:
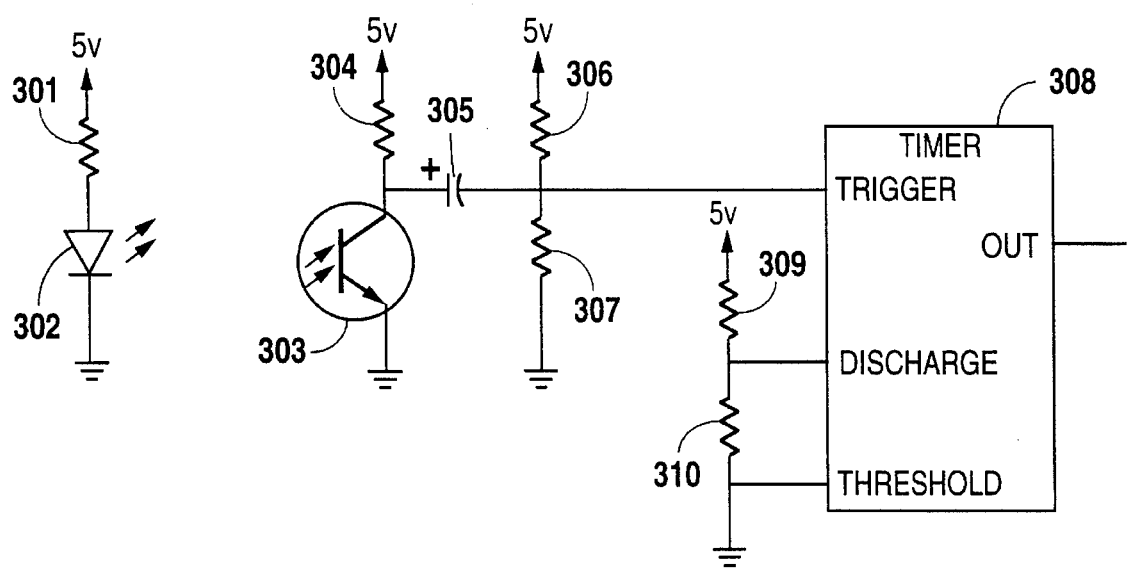
FIG. 7 is a schematic diagram of an alternate preferred embodiment of REM detection circuitry in the present invention.

Referring now to FIG. 7, yet another method of REM detection is embodied. LED 302 is maintained at some constant level of brightness set by resistor 301. The current out of phototransistor 303 is set by resistor 304, and is used to discharge capacitor 305. When eye movement causes discharge to occur, timer 308 is allowed to cycle and indicates to the rest of the electronics 580 that valid REM has been detected.

Figure 8:
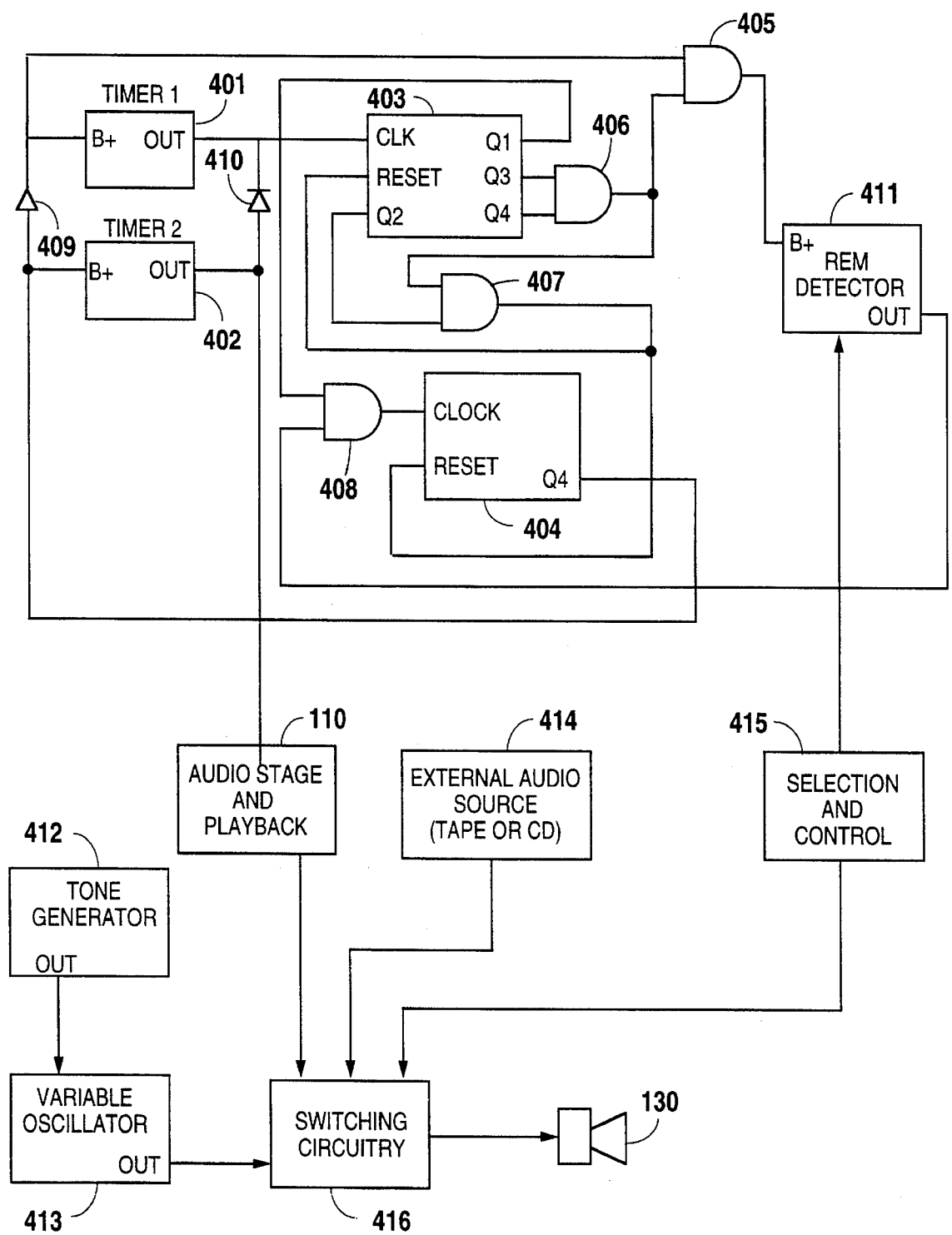
FIG. 8 is a block diagram of an alternate preferred embodiment of the present invention.

Referring now to FIG. 8, it can be seen that another addition to the system can be a longer recorded message, such as a language-teaching tape recording, activated by the dream state device 500 to play at some time after the cuing message has been initiated. In actual use, the tape recorder or CD player 414 could be connected to the headband electronics 580 by means of an audio jack located on the top of the headband pouch 550. This recorded message could either play once, upon completion of the cuing message, or it could be triggered to start and play continuously during the entire sleep time. Alternatively, this long recorded message could be played at a subliminal level instead of a normal listening level, or could be switched to a subliminal level after being played one or more times at a normal listening level.

Another embodiment of the electronics 580 is also shown in FIG. 8. When power is applied to the electronics 580, output Q4 of counter 404 will be low. This line is inverted and used to provide power to timer 401, which cycles at a rate of approximately 0.25 hertz. When power is applied, timer 401 provides four second pulses to be counted by counter 403. When approximately 48 seconds have passed (as registered by a count of 12 on counter 403), outputs Q3 and Q4 of counter 403 will both be in a high (+5 V level) condition. AND gate 406 will then output a corresponding high level signal, which, when combined with the inverted signal of counter 404 signal Q4 at AND gate 405, will enable power to the REM detection circuitry 411. After four more seconds, output Q1 of counter 403 will transition to a high level. If there is eye movement at this time, a pulse output from the REM detector circuit 411 will be combined with the Q1 output of counter 403 via AND gate 408 to restart the four second cycle of timer 401 and to pulse the clock input of counter 404, which cycles to control whether timer 401 or timer 402 is active. Timer 402 cycles at a selected rate of between 1 and 10 minutes.

If no REM is detected, and output Q1 of counter 403 has gone high, the next pulse from timer 401 will send output Q2 of counter 403 into a high level. The high level signal at output Q2 of counter 403, combined with the output of AND gate 406, operates to reset both counter 403 and counter 404. However, if counter 404 is allowed to accumulate 8 pulses from the REM detection circuitry 411, output Q4 of counter 404 will go into a high state. This will act to disable (turn off) timer 401 and enable (turn on) timer 402. When timer 402 has completed its cycle, it will operate to enable message playback by the audio storage and playback module 110 and reset counter 403 and counter 404.

Thus it is seen how applicants' dream detection device provides a small, portable, self-enclosed means, including typically a headband for a user to wear while sleeping to aid the sleeper in becoming lucid in his/her dream state. Its compact, user-friendly circuitry provides a cuing message after the detection of REM sleep. It further provides optional features, such as a REM detector capable of discriminating between eye positions, therefore allowing the possibility of the lucid dreamer to communicate or signal a playback device to selectively play back certain messages. It further provides the option of playing prerecorded messages, such as sounds mimicking alpha, beta, delta, and/or theta waves, to help induce sleep states. Importantly, all of the features and advantages described are capable of being enclosed in a headband or small case fittable to the wearer without inhibiting movement normal to the sleeping individual. Further, it is noted that applicants' use of the audio playback circuitry anticipates recording, storing, and playing back messages not only in the audible form, but messages such as light patterns for transmitting to an individual's closed eye or regulated tactile stimulation. In the typical mode, however, the message relayed to a sleeping individual is in the form of a stored audio message.

Terms such as "left," "right," "up," "down," "bottom," "top" "front," "back" "in" "out" and like are applicable to the embodiments shown and described in conjunction with the drawings. These terms are merely for purposes of description and do not necessarily apply to the position or manner in which the invention may be constructed for use.

Although the invention has been described in connection with the preferred embodiment, it is not intended to limit the invention's particular form set forth, but on the contrary, it is intended to cover such alternatives, modifications, and equivalences that may be included in the spirit and scope of the invention as defined by the appended claims.

What is claimed is:

1. A device to aid in inducing a lucid dream state, the device comprising;

means for detecting movement of an eye and for transmitting an eye movement signal in response thereto;

means for receiving and evaluating the eye movement signal to determine a REM or non-REM sleep condition, said receiving and evaluating means including means to emit a signal representative of the REM sleep condition of the individual when the frequency of the eye movement signal received by said receiving means exceeds a preselected number for a preselected period of time;

means for relaying prerecorded messages to the individual, said relaying means in operative engagement with the emitting means of said receiving and evaluating means; and a headband unit for locating said detecting means, said receiving and evaluating means, and said relaying means therein.

2. The device of claim 1, wherein the means for detecting includes discriminating means, said discriminating means for determining the relative position of the eye of the individual.

3. The device of claim 1, wherein said detecting means includes a light emitter and means positioned to receive light issuing from the light emitter, which light has been reflected from the closed eye of the sleeping individual.

4. The device of claim 3, wherein the receiver means includes a multiplicity of light radiation detection units.

5. The device of claim 4, wherein the multiplicity of radiation detection units are symmetrically arranged about the receiver means.

6. The device of claim 5, wherein the multiplicity of light radiation detection units are operatively engaged with a comparator for comparing the difference in radiation received by the units.

7. The device of claim 1, wherein said detecting means includes a light radiation emitter and a regulator to control the brightness of the emitter as a function of the distance between said detection means and the surface of the eye.

8. The device of claim 1, wherein said means for storing and relaying prerecorded messages includes means for recording and replaying audio messages.

9. The device of claim 8, wherein said means for storing and relaying prerecorded audio messages includes a means for modulating the recorded and relayed audio messages.

10. The device of claim 3 further including regulator means to control the intensity of the light issuing from the light emitter.

11. The device of claim 1 wherein said relaying means includes means for providing audio signals playable to the user, the audio messages capable of selective modulation, said means capable of manual activation by the user.

12. A method of communicating with an individual in the sleep state to aid in attaining lucidity in the dream state, the method comprising the steps of:

providing in a user-wearable headband a device comprising means for detecting movement of an eye and for transmitting an eye movement signal in response thereto; means for receiving and evaluating the eye movement signal to determine a REM or non-REM sleep condition, said receiving and evaluating means including means to emit a signal representative of the REM sleep condition of the individual when the frequency of the eye movement signal received by said receiving means exceeds a preselected number for a preselected period of time; and means for relaying prerecorded messages to the individual, said relaying means in operative engagement with the emitting means of said receiving and evaluating means;

recording on the device messages to be communicated to the sleeping individual;

placing the headband on the individual's head;

entering a sleeping condition;

detecting eye movement of the sleeping individual;

analyzing the eye movement to determine the sleep state of the individual; and relaying prerecorded messages to the individual in response to the sleep state of the individual.

13. The method of claim 12 further including the step of setting the intensity at which the recorded messages will be communicated, such setting step to follow the recording step.

14. The method of claim 13, wherein the recorded messages of the recording step comprises a sound signal.

15. The method of claim 13, wherein the setting step further includes the step of setting the volume below the individual's audible threshold.

16. The method of claim 14, wherein the recording step includes the step of recording messages in the individual's own voice.

17. The method of claim 12, wherein the device of the providing step includes the step of providing the device wherein said eye detection movement means includes a means to determine eye position, the eye position determining means engaging the relaying means of said device to selectively control the messages to be relayed to the individual.

18. The method of claim 17 further including the step of signaling said device through movement of the eye to selectively relay certain messages to the sleeping individual.

19. The method of claim 12 further including the step of manually activating the relaying means, the manually activating step occurring prior to the step of entering the sleeping condition.

20. The method of claim 19, wherein the sound produced by the manually-activated relaying means varies in frequency.

21. The method of claim 20, wherein the frequency pattern mimics sleep state progression from an awake condition to REM.

22. The method of claim 13, wherein the messages of said recording step are visual.

23. The method of claim 13, wherein the messages of said recording step are tactile.

* * * * *